United States Patent
Schmieding et al.

(10) Patent No.: US 8,663,324 B2
(45) Date of Patent: *Mar. 4, 2014

(54) DOUBLE SOCKET ACL RECONSTRUCTION

(75) Inventors: Reinhold Schmieding, Naples, FL (US); Jacob Jolly, Naples, FL (US)

(73) Assignee: Arthrex, Inc., Naples, FL (US)

( * ) Notice: Subject to any disclaimer, the term of this patent is extended or adjusted under 35 U.S.C. 154(b) by 205 days.

This patent is subject to a terminal disclaimer.

(21) Appl. No.: 12/165,107

(22) Filed: Jun. 30, 2008

(65) Prior Publication Data

US 2009/0018654 A1    Jan. 15, 2009

Related U.S. Application Data

(60) Provisional application No. 60/947,290, filed on Jun. 29, 2007.

(51) Int. Cl.
*A61F 2/08*  (2006.01)
*A61B 19/00*  (2006.01)
*A61B 17/00*  (2006.01)

(52) U.S. Cl.
USPC .............. 623/13.14; 623/13.13; 623/13.2; 606/79; 128/898

(58) Field of Classification Search
USPC .......... 623/13.11–13.14, 13.17–13.2; 606/79, 606/80, 88, 96, 104, 228, 232
See application file for complete search history.

(56) References Cited

U.S. PATENT DOCUMENTS

| | | | |
|---|---|---|---|
| 5,306,301 A | 4/1994 | Graf et al. | |
| 5,603,716 A | 2/1997 | Morgan et al. | |
| 6,517,578 B2 * | 2/2003 | Hein | 623/13.13 |
| 6,533,802 B2 * | 3/2003 | Bojarski et al. | 606/232 |
| 6,716,234 B2 | 4/2004 | Grafton et al. | |
| 2003/0050667 A1 * | 3/2003 | Grafton et al. | 606/228 |
| 2003/0216780 A1 * | 11/2003 | Fitts et al. | 606/232 |
| 2004/0199166 A1 | 10/2004 | Schmieding et al. | |
| 2005/0149118 A1 * | 7/2005 | Koyfman et al. | 606/228 |
| 2008/0046009 A1 | 2/2008 | Albertorio et al. | |
| 2008/0234819 A1 | 9/2008 | Schmieding et al. | |

* cited by examiner

*Primary Examiner* — David Isabella
*Assistant Examiner* — Yashita Sharma
(74) *Attorney, Agent, or Firm* — Dickstein Shapiro LLP

(57) ABSTRACT

An all-inside double-socket ACL reconstruction technique, according to which a femoral socket and a closed tibial socket are provided to accommodate retrograde fixation of at least one graft (for example, a semitendonosus allograft) within the sockets. The closed tibial socket is formed by using a retrograde drill device provided with a retrograde drill cutter detachable from a retrograde drill guide pin. The femoral socket may be formed by the retrograde drill method or by a conventional method, and may be carried out before or after the formation of the tibial socket. The graft is secured in the knee by employing a transversal implant, or by employing an interference screw, and/or a continuous loop/button construct.

6 Claims, 24 Drawing Sheets

DOUBLE SOCKET ACL RECONSTRUCTION

CROSS REFERENCE TO RELATED APPLICATIONS

This application claims the benefit of U.S. Provisional Application Ser. No. 60/947,290 filed on Jun. 29, 2007, the entire disclosure of which is incorporated by reference in its entirety herein.

FIELD OF THE INVENTION

The present invention relates to the field of surgery and, more particularly, to methods of reconstructive knee surgeries.

BACKGROUND OF THE INVENTION

Reconstructive knee surgeries, particularly anterior cruciate ligament (ACL) reconstruction, are well-known in the art. In general, these methods of tenodesis involve drilling a tunnel through the tibia, drilling a closed tunnel (socket) into the femur, inserting a substitute ACL graft into the tunnels, and securing the grafts to the walls of the tibial and femoral tunnels using interference screws or the like.

One drawback of the described methods of ACL reconstruction is that the formation of the tibial tunnel involves removal of significant amounts of bone material. U.S. Pat. No. 5,603,716 discloses a technique for ACL reconstruction that avoids the above-noted problem by forming sockets in both the femur and the tibia using a coring bone harvester. The harvester is impacted into bone to a desired depth so that bone material collects as a bone core within the harvester tube. The bone core is extracted from the bone socket using a simultaneous twisting and pulling motion. Such harvesting of bone cores in the joint is technically difficult.

Accordingly, the need exists for a method of ACL reconstruction that provides tibial and femoral socket formation without the need for extracting a bone core to form a bone socket and to avoid drilling through growth plates in skeletally immature patients. There is also a need for a minimally invasive method of ACL reconstruction that provides drilling of femoral and tibial sockets independently of one another and minimizes incisions of distal cortices and reduces intraarticular bone fragmentation of tunnel rims.

BRIEF SUMMARY OF THE INVENTION

The present invention provides techniques and reconstruction systems for ligament or tendon repair. The invention provides a technique for forming femoral and tibial closed sockets, and subsequently securing a graft in these sockets, in an all-inside manner and with minimally-invasive ACL reconstruction through three portals. The present invention also provides an all-inside double socket ACL reconstruction with improved cosmesis, strong and stiff fixation options, which in turn improve patient morbidity and hasten rehabilitation.

Other features and advantages of the present invention will become apparent from the following description of the invention which refers to the accompanying drawings.

DETAILED DESCRIPTION OF THE INVENTION

Figure 1:
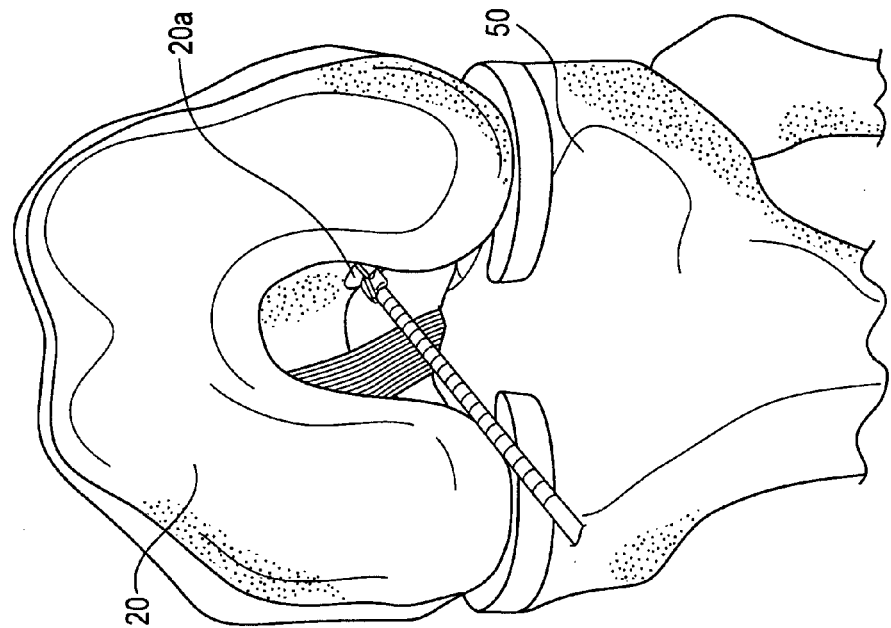
FIGS. 1 and 2 illustrate subsequent steps for the femoral socket formation through the anteromedial portal during an all-inside double socket ACL reconstruction according to an exemplary embodiment of the present invention.

The present invention provides techniques and reconstruction systems for ligament or tendon repair. The invention provides a technique for forming femoral and tibial closed bone sockets, and subsequently securing a graft in these sockets, in an all-inside manner and with minimally-invasive ACL reconstruction through three portals. The present invention also provides an all-inside double socket ACL reconstruction with improved cosmesis, strong and stiff fixation options, which in turn improve patient morbidity and hasten rehabilitation.

According to the all-inside double socket ACL reconstruction for ligament repair of the present invention, a femoral socket and a closed tibial socket are provided to accommodate retrograde fixation of a graft (for example, a semitendonosus allograft) within the two sockets. The tibial closed socket may be formed by using a retrodrill device provided with a retrodrill cutter detachable from a threaded guide pin, in the manner described in U.S. Patent Application Publication No. 2004/0199166, entitled "ACL Reconstruction Technique Using Retrodrill," the disclosure of which is incorporated by reference herein in its entirety. The femoral tunnel or socket may be formed by a conventional method through the anteromedial portal or by other method (for example, by a retrodrill method), and may be carried out before or after the formation of the tibial socket.

Anatomic femoral fixation of the graft may be accomplished by employing a transversal implant (for example, a Medial Portal TransFix Implant) or by employing an interference screw (for example, a RetroScrew) and/or a continuous loop/button construct (for example, a suture loop/button construct such as Arthrex's RetroButton). Anatomic tibial fixation of the graft may be accomplished by employing an interference screw (for example, a RetroScrew) and/or a continuous loop/button construct (for example, a suture button such as Arthrex's RetroButton).

Preparation of the graft (for example, a semitendonosus allograft) may be conducted by employing a continuous loop/button construct provided with a button (preferably of metal such as titanium alloy) and a continuous loop attached to the button (such as Arthrex's RetroButton). The button has an oblong configuration and a width that is preferably less than about 1 mm narrower than the width of the drill hole through which the button is inserted and subsequently passed through. The button is provided with an inside eyelet that allows the passage of the continuous loop.

The method of ACL reconstruction according to the present invention comprises, for example, the steps of: (i) drilling at least a femoral and tibial socket using a retrodrill technique; (ii) providing a graft (soft tissue graft or BTB graft) in the vicinity of the sockets; and (iii) securing the graft within the femoral and tibial sockets.

According to yet another embodiment, a method of ACL reconstruction of the present invention comprises, for example, the steps of: (i) forming a femoral socket through the anteromedial portal in the femur; (ii) forming a closed tibial socket using a retrodrill technique; (iii) providing a graft (soft tissue graft or BTB graft) in the vicinity of the sockets; (iv) securing the graft (soft tissue graft or BTB graft) in the femoral socket by employing one of a transversal implant, an interference screw and/or a continuous loop/button construct; and (v) securing the graft (soft tissue graft or BTB graft) in the tibial socket.

The techniques and reconstruction systems for ligament or tendon repair of the present invention eliminate the formation of tibial tunnels and provide a simpler ACL reconstruction technique. The methods allow proper tensioning and fixation of grafts in an all-inside double socket ACL reconstruction technique, wherein formation of tibial tunnels is eliminated and graft fixation is improved.

Figure 2:
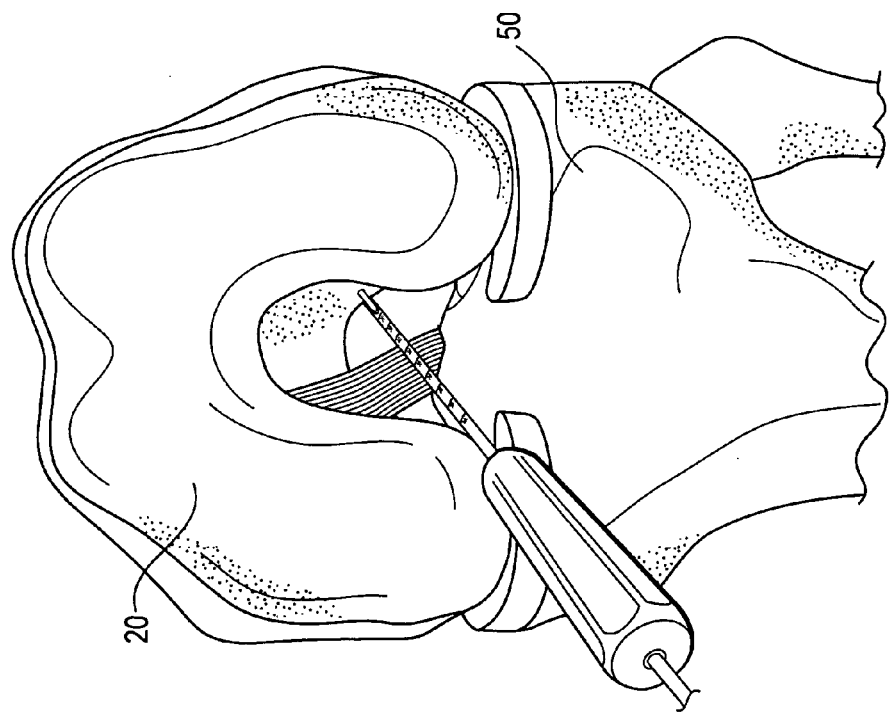

A more detailed explanation of the instrumentation and steps of an all-inside double socket ACL reconstruction technique of the present invention is provided below (with reference to the corresponding Figures):

FIGS. 1 and 2—Femoral Socket Formation Through the Anteromedial Portal

As detailed below, the femoral tunnel or socket may be formed in an antegrade manner through the anteromedial portal or by other method (for example, a retrodrill method), and may be carried out before or after the formation of the tibial socket.

FIGS. 1 and 2 illustrate the formation of a femoral socket or tunnel 20a through femur 20. Using the anteromedial portal to form the femoral socket allows anatomic placement and facilitates fixation using interference screws, transversal implants or suture loop/button constructs.

For anteromedial portal socket creation, the knee is hyperflexed and a guide (e.g., a Transtibial ACL Drill Guide (TTG)) is used through the anteromedial portal to place a pin (e.g., a Beath Pin), as shown in FIG. 1 (if using RetroButton fixation, use RetroButton Pin). A reamer (e.g., a Cannulated Headed Reamer) may be placed over the pin for creation of the femoral socket 20a (FIG. 2). A cannula (e.g., a Shoehorn™ Cannula) may be useful in passing the headed reamer into the joint. The pin (e.g., the Beath Pin or RetroButton Pin) may be used to pass a graft passing suture or button passing suture.

Figure 3A:
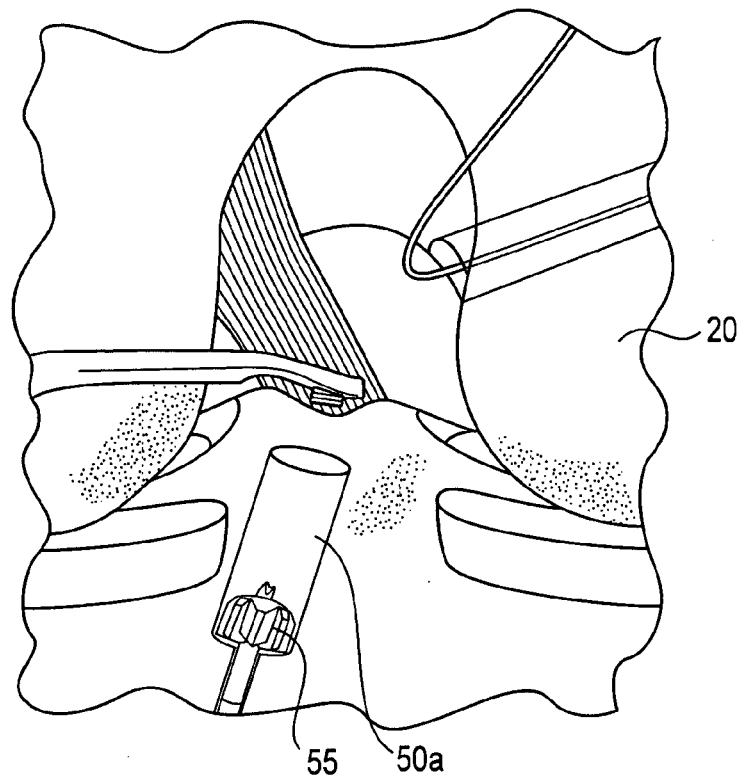
FIGS. 3-5 illustrate subsequent steps for the tibial socket formation during an all-inside double socket ACL reconstruction according to an exemplary embodiment of the present invention.
Figure 3B:
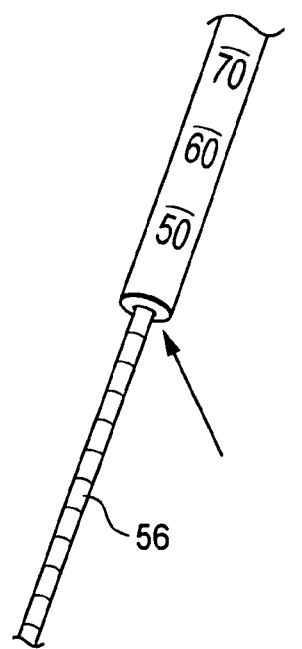
Figure 3C:
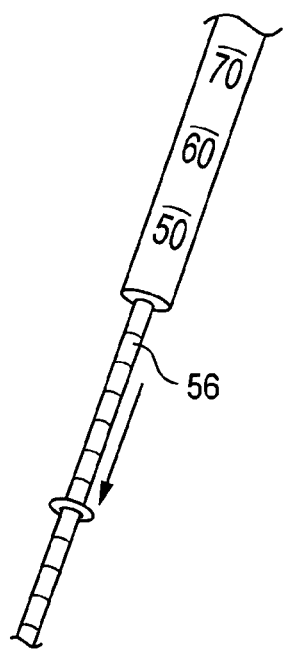
Figure 4:
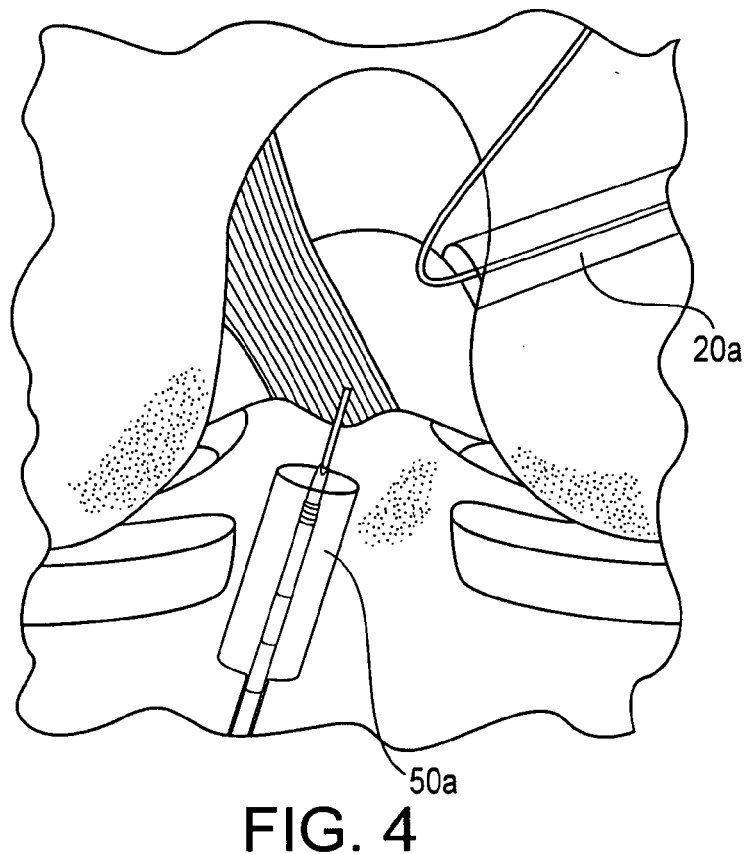
Figure 5:
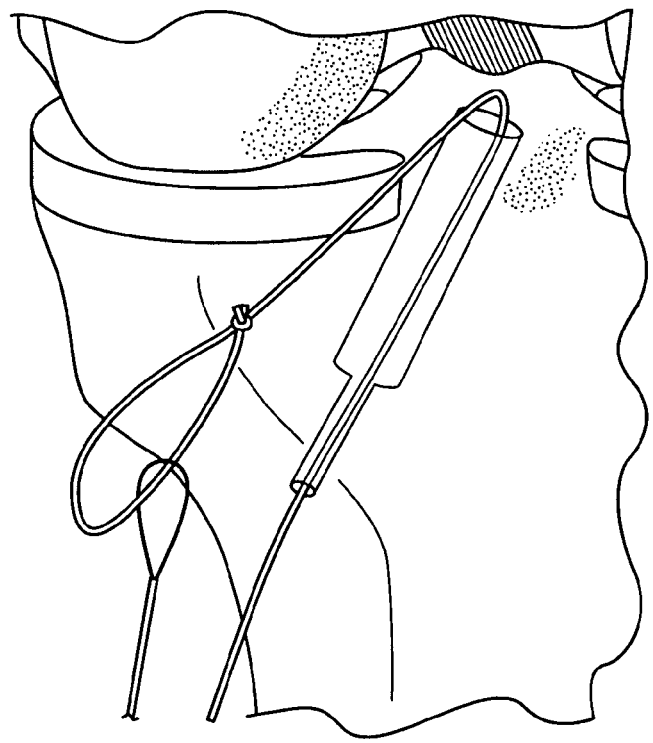

FIGS. 3-5—Tibial Socket Formation

As described in more detail below, the tibial socket may be formed by using a retrodrill device provided with a retrodrill cutter detachable from a threaded guide pin.

FIGS. 3-5 illustrate the formation of a tibial socket 50a in tibia 50, prior or subsequent to the formation of the femoral socket 20a. The tibial socket 50a is preferably formed using a retrodrill cutter 55 (FIG. 3(b)) which is inserted in a retrograde manner through tibia 50, and as detailed in U.S. Patent Application Publication No. 2004/0199166, entitled "ACL Reconstruction Technique Using Retrodrill." As described in U.S. Patent Application Publication No. 2004/0199166, the retrograde drill cutter is inserted in a retrograde manner through tibia 50 by employing a retrograde drill guide pin 56 provided with depth markings.

The RetroDrill guide is placed over the tibial ACL footprint. The drill sleeve is pushed down to bone. The intraosseous length on the drill sleeve where it exits the drill guide is noted. The RetroDrill guide pin is drilled through the tibia and into the joint. A retrodrill cutter 55 (e.g., a RetroCutter™) is engaged onto the pin. The black rubber ring is pushed to the end of the drill sleeve (FIG. 3(a)). The socket depth on the guide pin 56 is noted as the socket is created (FIG. 3(b)). The tibial socket is drilled approximately 10-15 mm less than the length of the tibia 50 to maximize socket length and guarantee sufficient space for graft tensioning.

A suture strand (e.g., a #2 FiberStick™) is passed through the cannulation of the retrodrill guide pin (FIGS. 4 and 5). A grasper is then used to bring the suture out of the anteromedial portal and the pin is removed from the tibia. The FiberStick is tied around the Nitinol wire loop.

Figure 33:
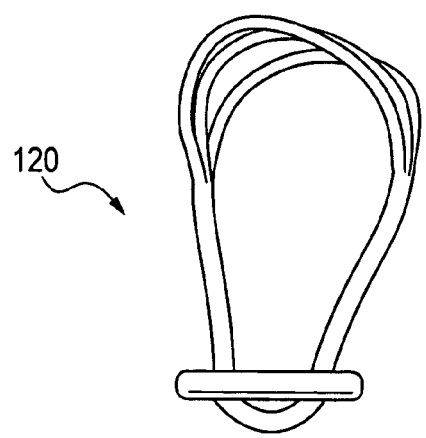
FIGS. 33 and 34 illustrate a continuous loop/button construct used for fixating a graft according to the all-inside double socket ACL technique of the present invention.
Figure 34:
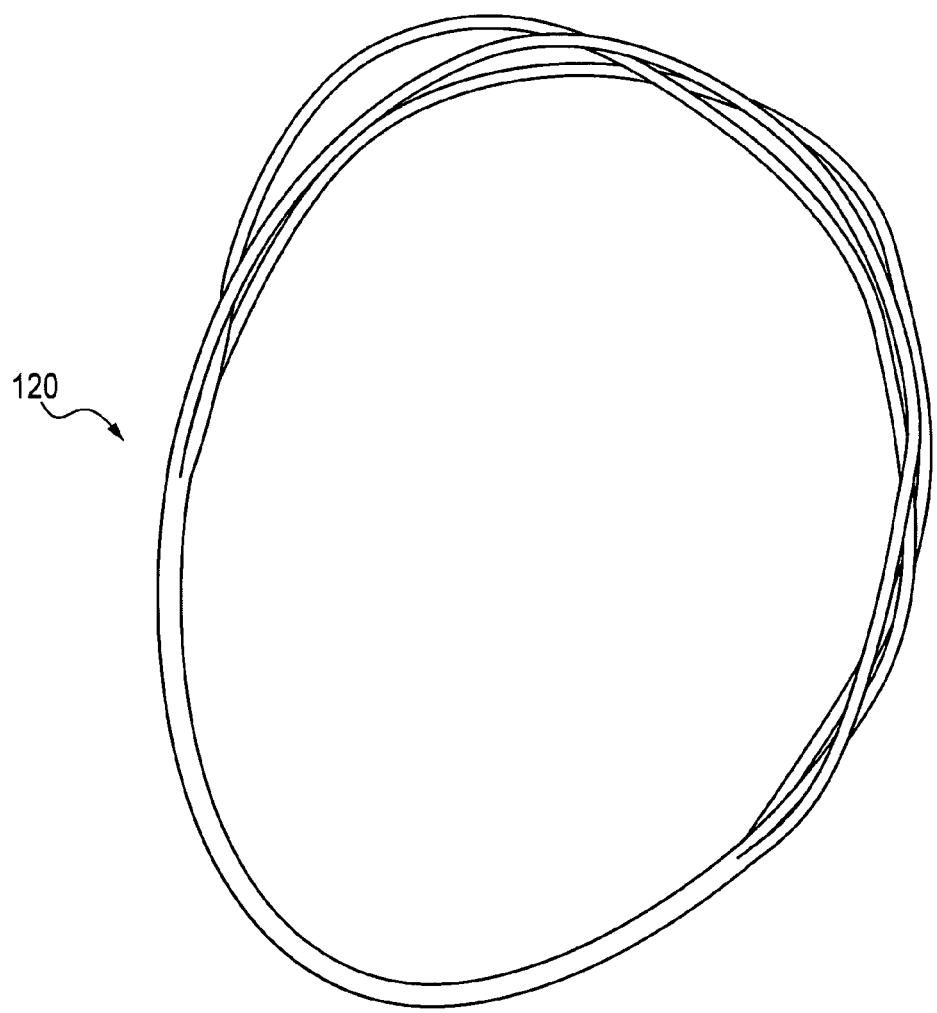

Once the femoral and tibial tunnels or sockets have been completed, graft insertion and fixation may be subsequently carried out. Preparation of the allograft may be conducted by employing a continuous loop/button construct 120 (FIGS. 33 and 34) provided with a button (preferably of titanium alloy) and a continuous loop attached to the button, as described in U.S. Ser. No. 11/889,740, filed Aug. 16, 2007, the disclosure of which is herein incorporated by reference. The button has an oblong configuration and a width that is preferably less than about 1 mm narrower than the width of the drill hole through which the button is inserted and subsequently passed through. The button is provided with an inside eyelet that allows the passage of the continuous loop. In an exemplary embodiment, the suture loop may be a single high strength suture such as FiberWire® suture, sold by Arthrex, Inc. of Naples, Fla., and described in U.S. Pat. No. 6,716,234, the disclosure of which is incorporated by reference herein. In another exemplary embodiment, the continuous loop may be formed of a plurality of suture strands configured to separate from a single strand to a plurality of strands in a continuous loop.

According to an exemplary embodiment of the present invention, the allograft (which may be a soft tissue graft) is folded in half over the loop of the button 200 and tension is applied. Subsequently, passing sutures are pulled and the graft is passed into the femoral and/or tibial socket. When the graft reaches the opening of the femoral/tibial socket on the bone cortex, a slight popping sensation may be felt as the button exits and begins to flip horizontally on the cortex. Distal traction on the graft and release of the passing sutures facilitate complete deployment of the button. The passing suture may be removed and graft fixation may be completed.

FIGS. 6-11—Graft Passing and Femoral Fixation

The anteromedial portal is used to pass the graft into the femoral and tibial sockets. As described below, anatomic femoral fixation of graft 60 may be accomplished in various ways, for example, by employing a transversal implant 110 (for example, a Medial Portal TransFix Implant) or by employing an interference screw 130 (for example, a RetroScrew) and/or the continuous loop/button construct 120 provided with a button and a continuous loop attached to the button (for example, a RetroButton).

Figure 6:
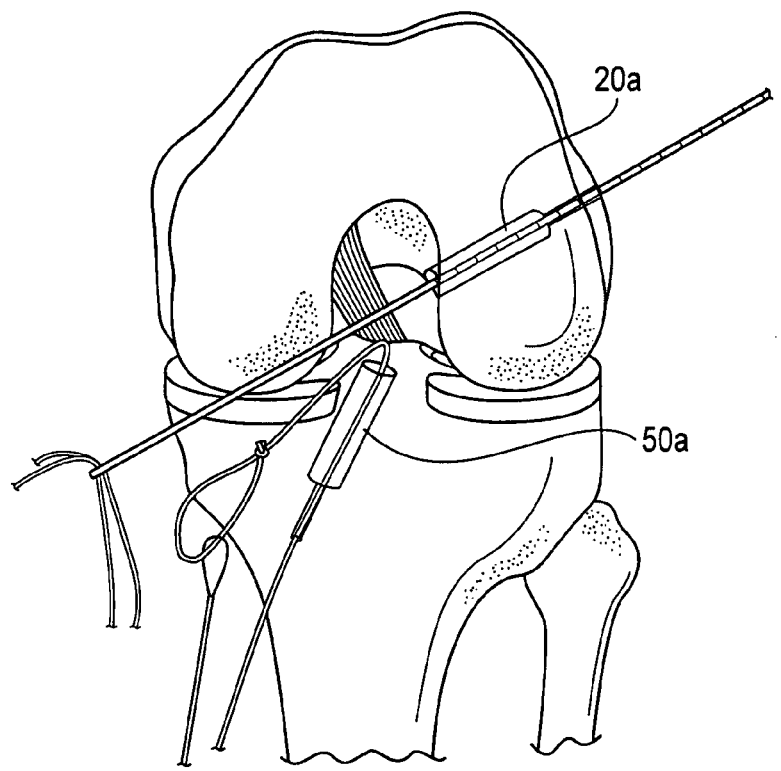
FIGS. 6-8 illustrate subsequent steps for graft passing and femoral fixation with a suture loop/button construct according to an exemplary embodiment of the present invention.
Figure 7:
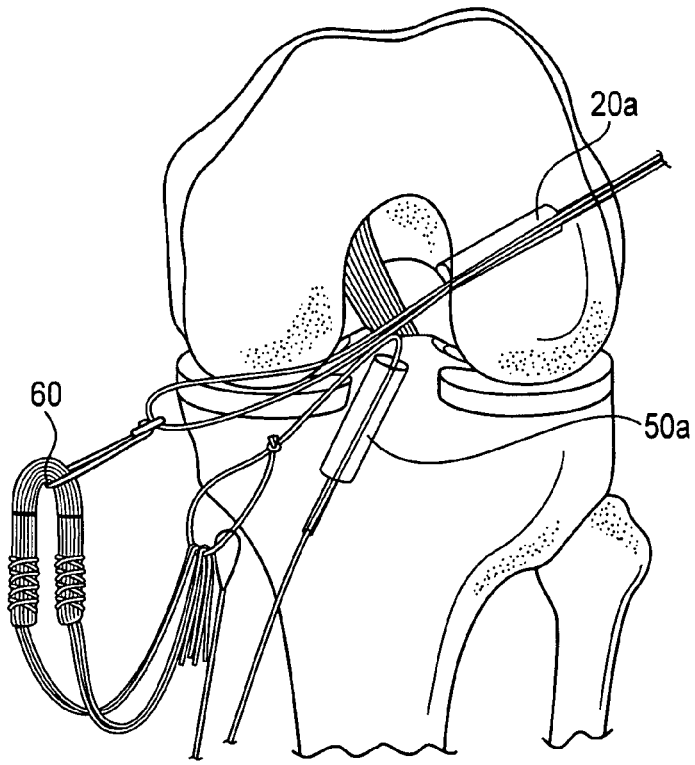
Figure 8:
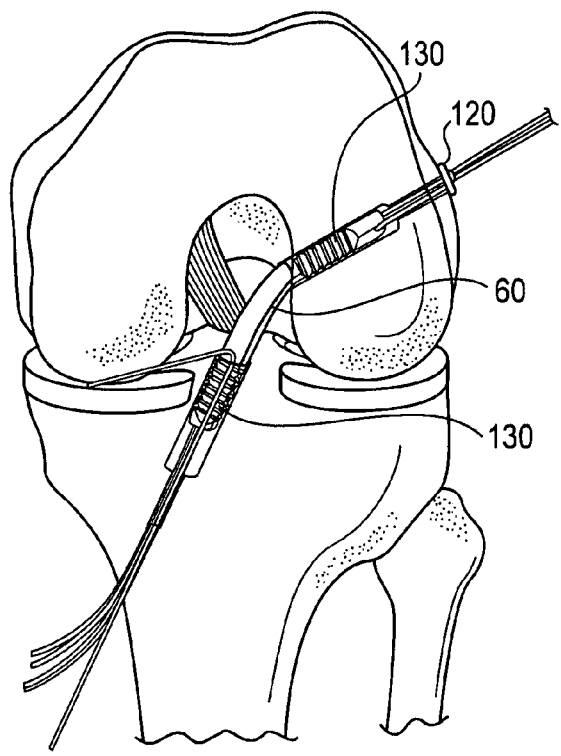

Referring to FIGS. 6-8, the passing suture of the suture/button construct may be passed through the femur 20 using a pin (e.g., a RetroButton Pin). The tibial suture loop, with the attached Nitinol wire, is used to pass the whipstitched graft sutures through the tibia. The femoral portion of the graft is first passed by pulling the button passing suture. When the line on the graft enters the femoral socket 20*a*, the button 120 deploys and the graft 60 is fixed within the femur 20. A femoral interference screw 130 may be inserted through the medial portal if desired, for aperture fixation. The tibial end of the graft is passed by pulling the tibial passing suture with wire attached. The wire should stay anterior to the graft during this process. This anterior position of the wire should preferably be maintained at all times.

Figure 9:
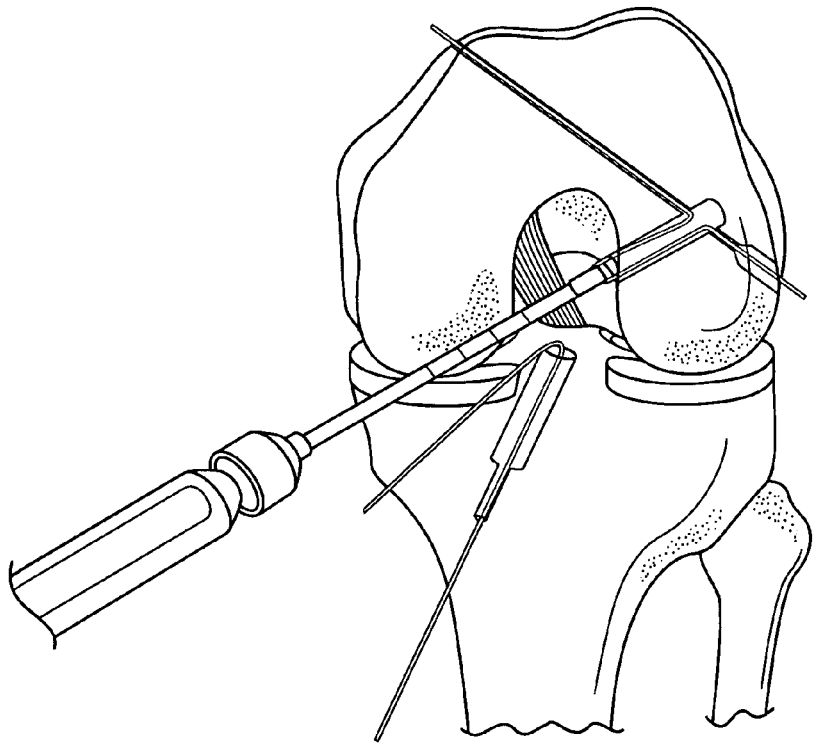
FIGS. 9-11 illustrate subsequent steps for graft passing and femoral fixation with a transversal implant according to an exemplary embodiment of the present invention.
Figure 10:
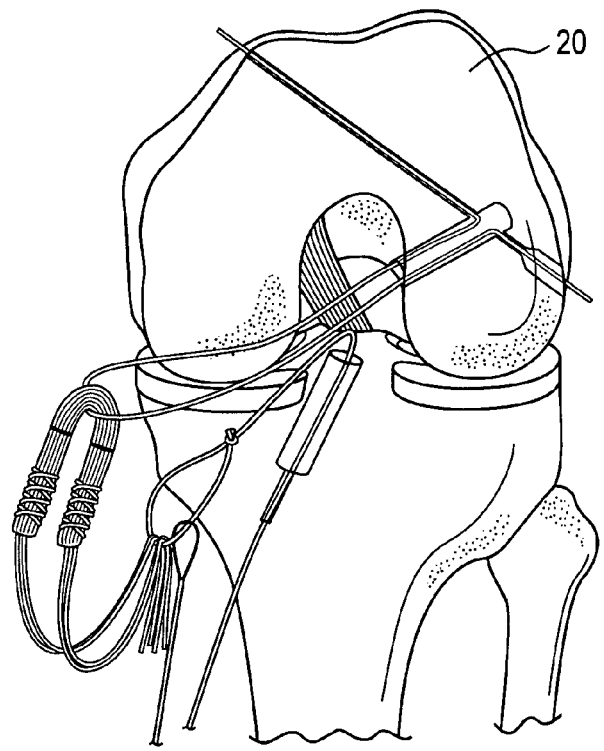
Figure 11:
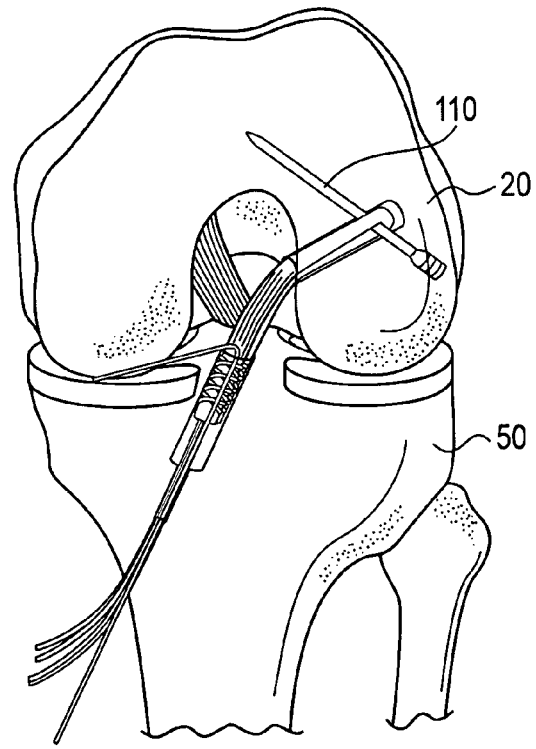
Figure 12:
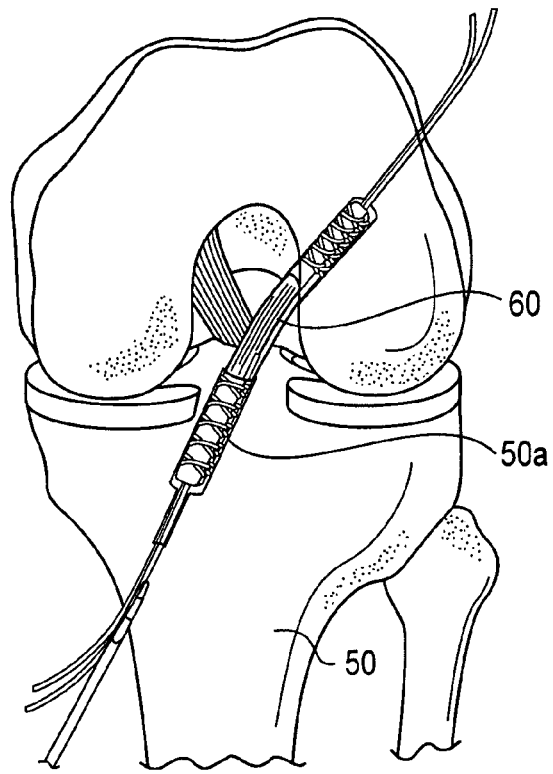
FIGS. 12-17 illustrate subsequent steps for graft passing and tibial fixation according to an exemplary embodiment of the present invention.
Figure 13:
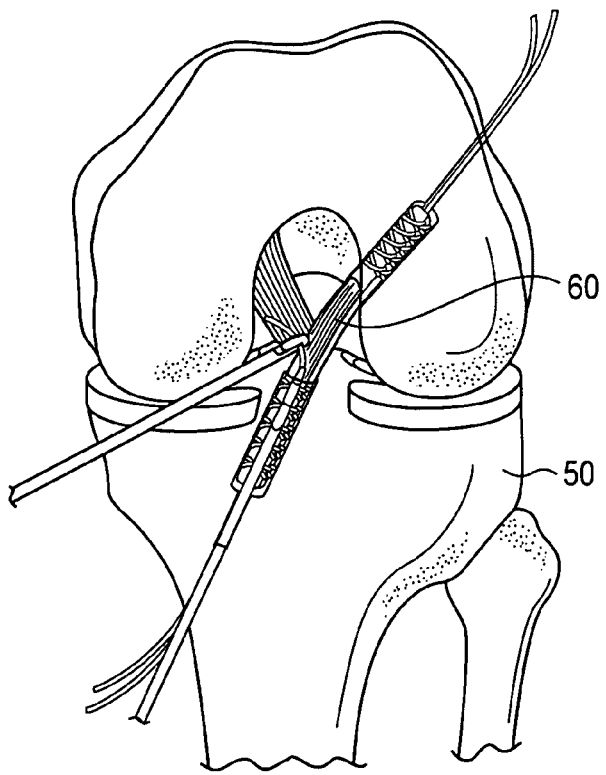
Figure 14:
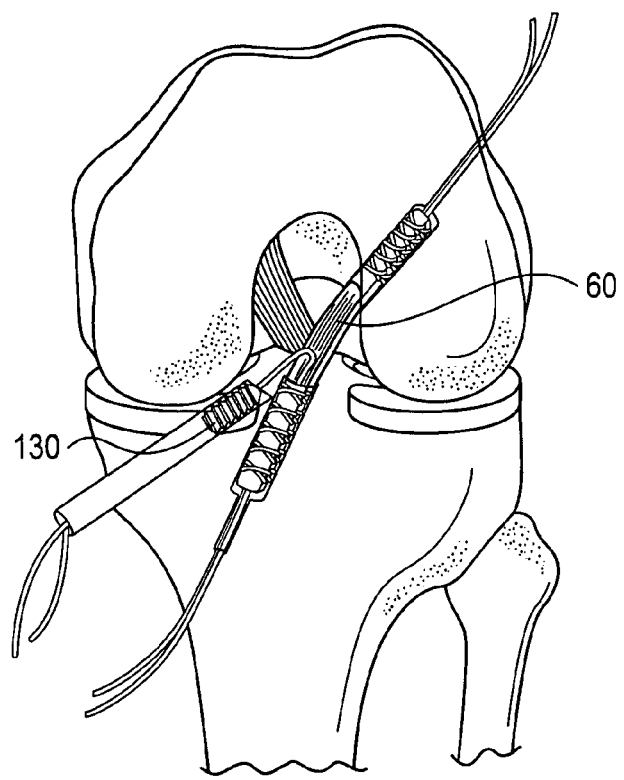

Referring to FIGS. 9-11, for Medial Portal TransFix, the graft passing wire is pulled out of the medial portal and load graft into the wire loop. The graft sutures are placed in the tibial suture loop. The femoral end of graft 60 is pulled into place with the Nitinol graft passing wire and the femur is fixed by inserting a transversal implant 110 (e.g., Bio-TransFix Implant 110). Graft suture tails are placed into the tibial passing suture loop. The distal end of suture is pulled to pass the tibial sutures and the Nitinol wire into the tibia, then the graft sutures are pulled to seat graft into tibial socket. The wire should be maintained anterior to the graft.

FIGS. 12-17—Tibial Fixation

Figure 15:
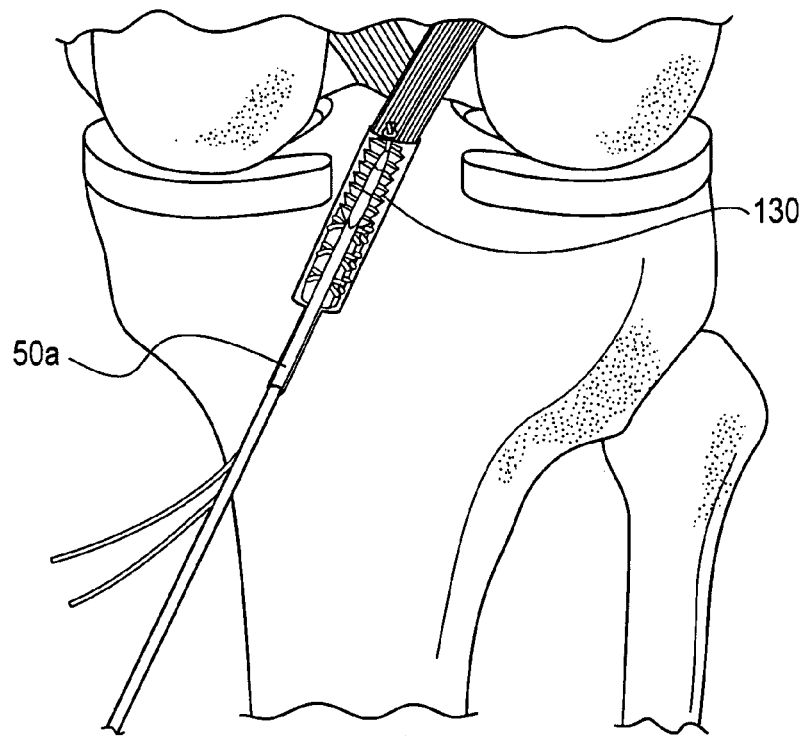
Figure 16:
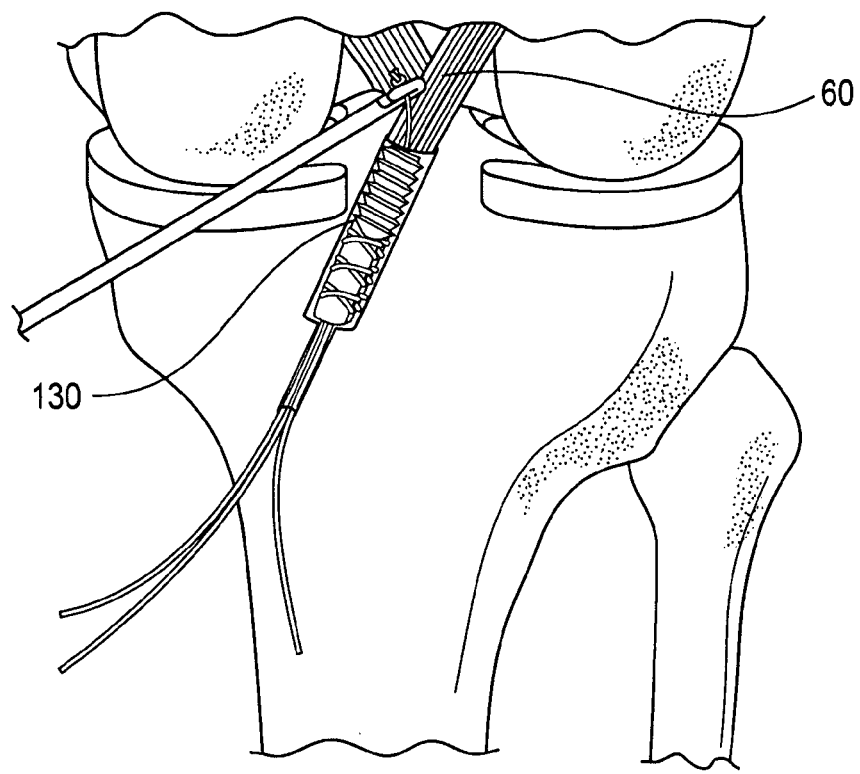
Figure 17:
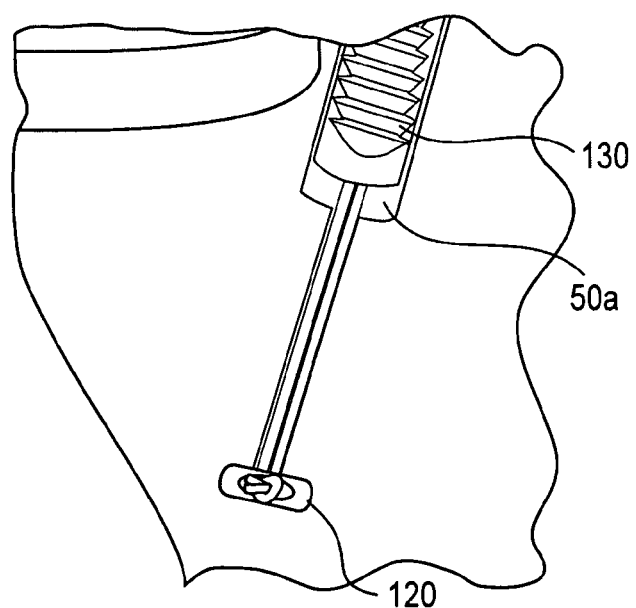

The wire is backed down until about 1 cm is visible in the joint. The graft 60 is tensioned and the knee is cycled. A driver (e.g., a RetroScrew Driver) is passed over the Nitinol wire until the tip of the driver is seen in the joint anterior to the graft. A suture wire (e.g., FiberStick) is passed into the driver and retrieved out of the anteromedial portal. A tibial interference screw 130 (RetroScrew 130) is loaded onto the suture wire (FiberStick) and a knot is tied behind the screw. A cannula (e.g., a Shoehorn Cannula) is used to pass the screw into the joint. The distal suture wire is pulled until the screw is vertical, then the driver tip is pushed into the screw cannulation (FIGS. 15-17). The suture wire (FiberStick) is tensioned distally and secured onto the handle. The graft is tensioned and the screw tip is pulled into the socket. The driver is turned counterclockwise until seated completely flush with the tibial plateau. A tamp (e.g., a RetroScrew Tamp) may be used to help seat the screw 130 and prevent graft-wrapping. The suture is released off the handle, the driver removed from the tibia and the suture wire (FiberStick) from the joint. Suture tails may be fixed over the cortex with a two-hole suture button 120 for backup fixation (FIG. 17).

Figure 18:
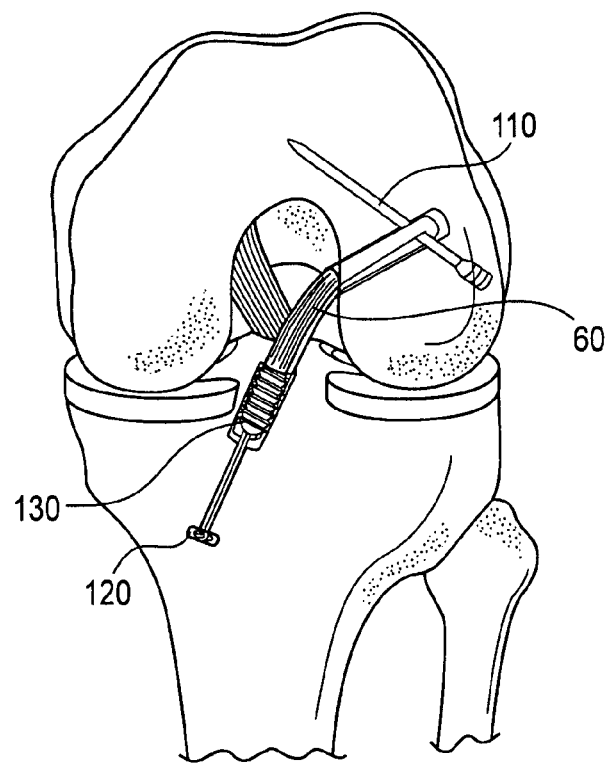
FIG. 18 illustrates a secured ACL graft by employing a transversal implant for femoral fixation.
Figure 19:
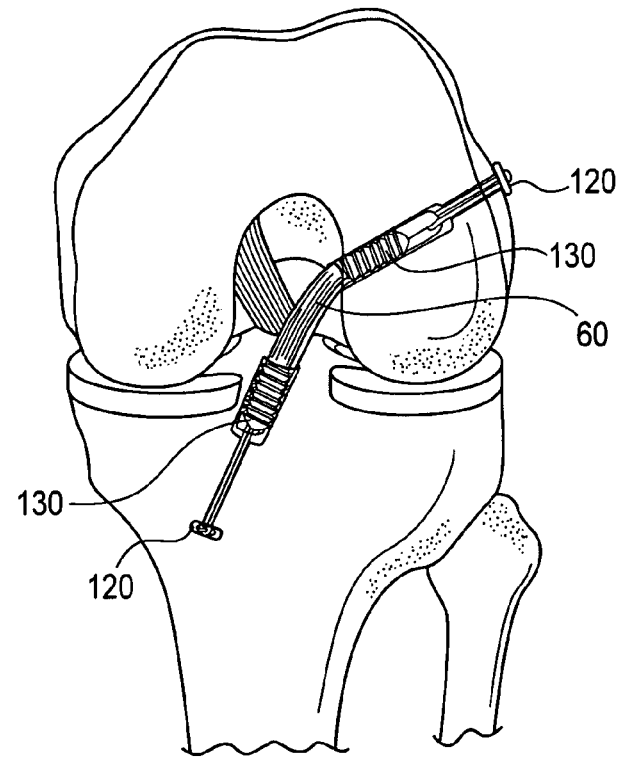
FIG. 19 illustrates a secured ACL graft by employing an interference screw and a suture loop/button construct for femoral fixation.
Figure 20:
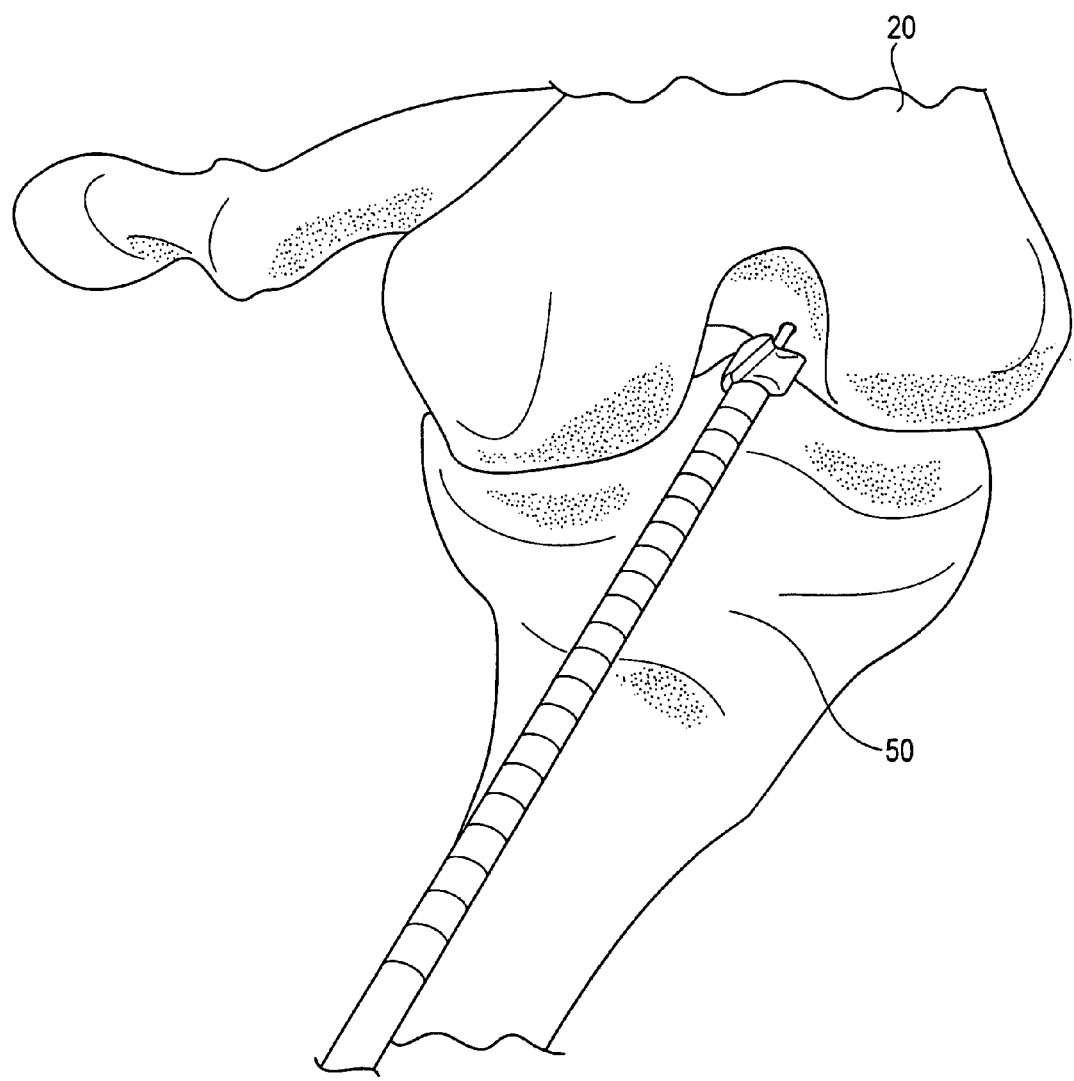
FIGS. 20-32 illustrate various steps of a method of an all-inside double socket ACL reconstruction according to an exemplary embodiment of the present invention.
Figure 21:
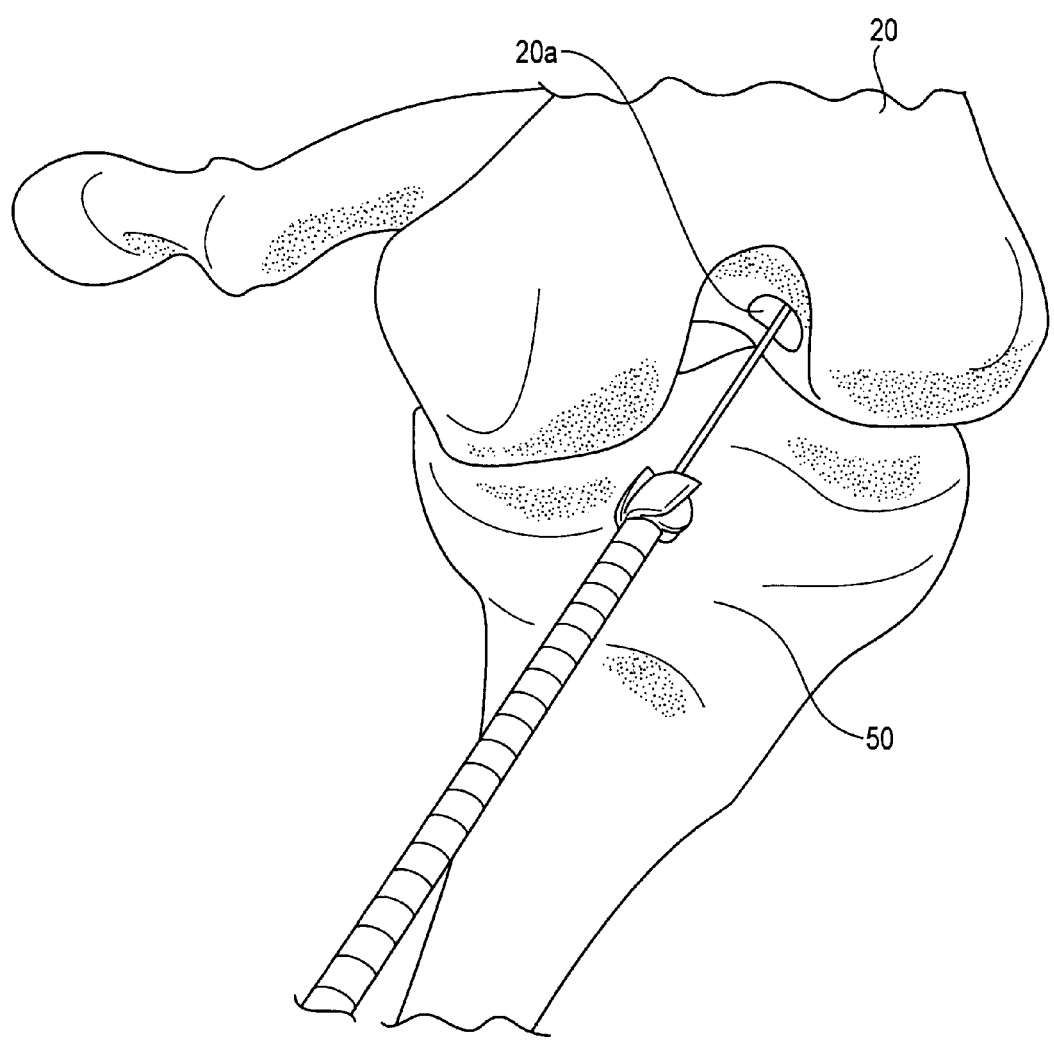
Figure 22:
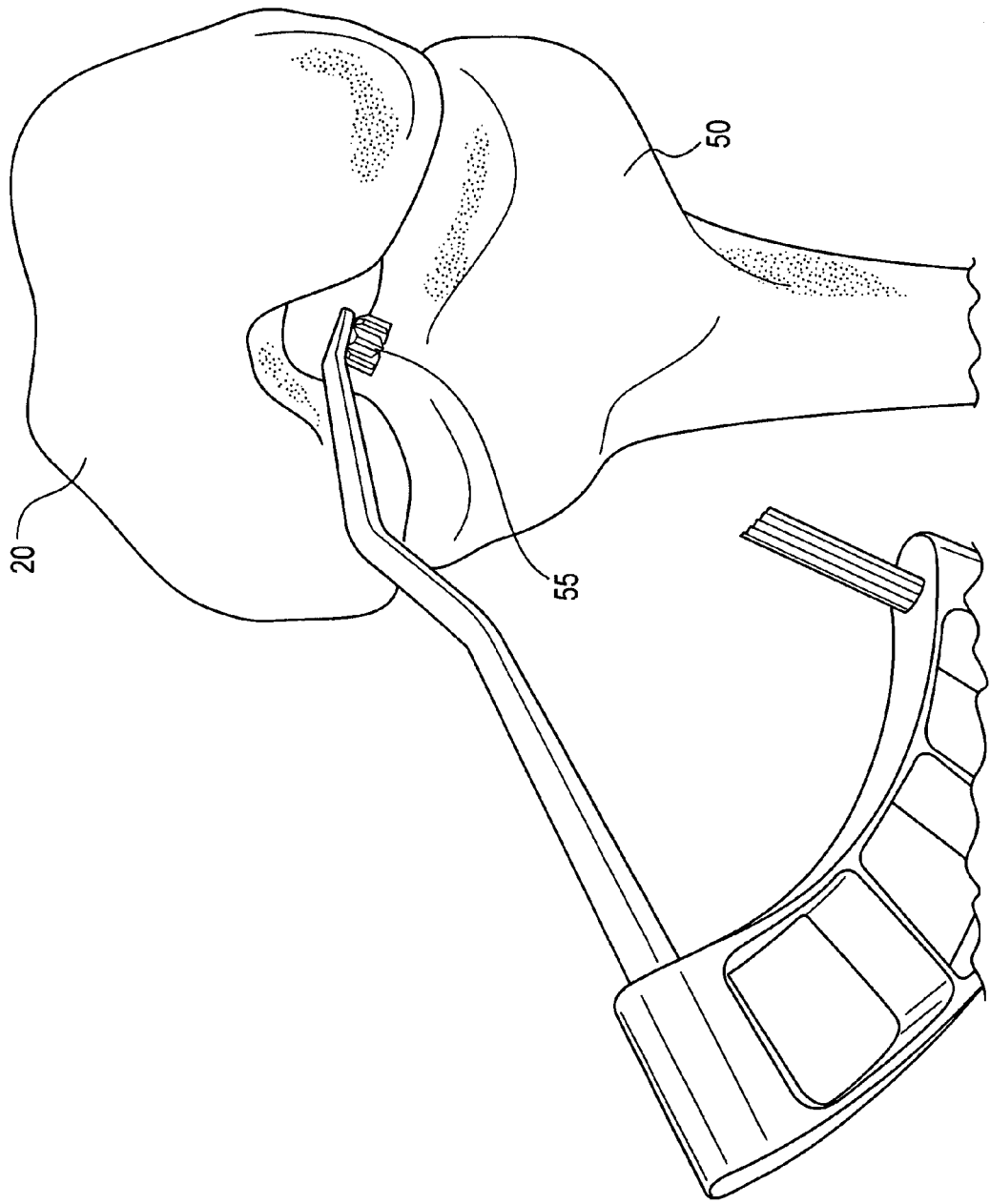
Figure 23:
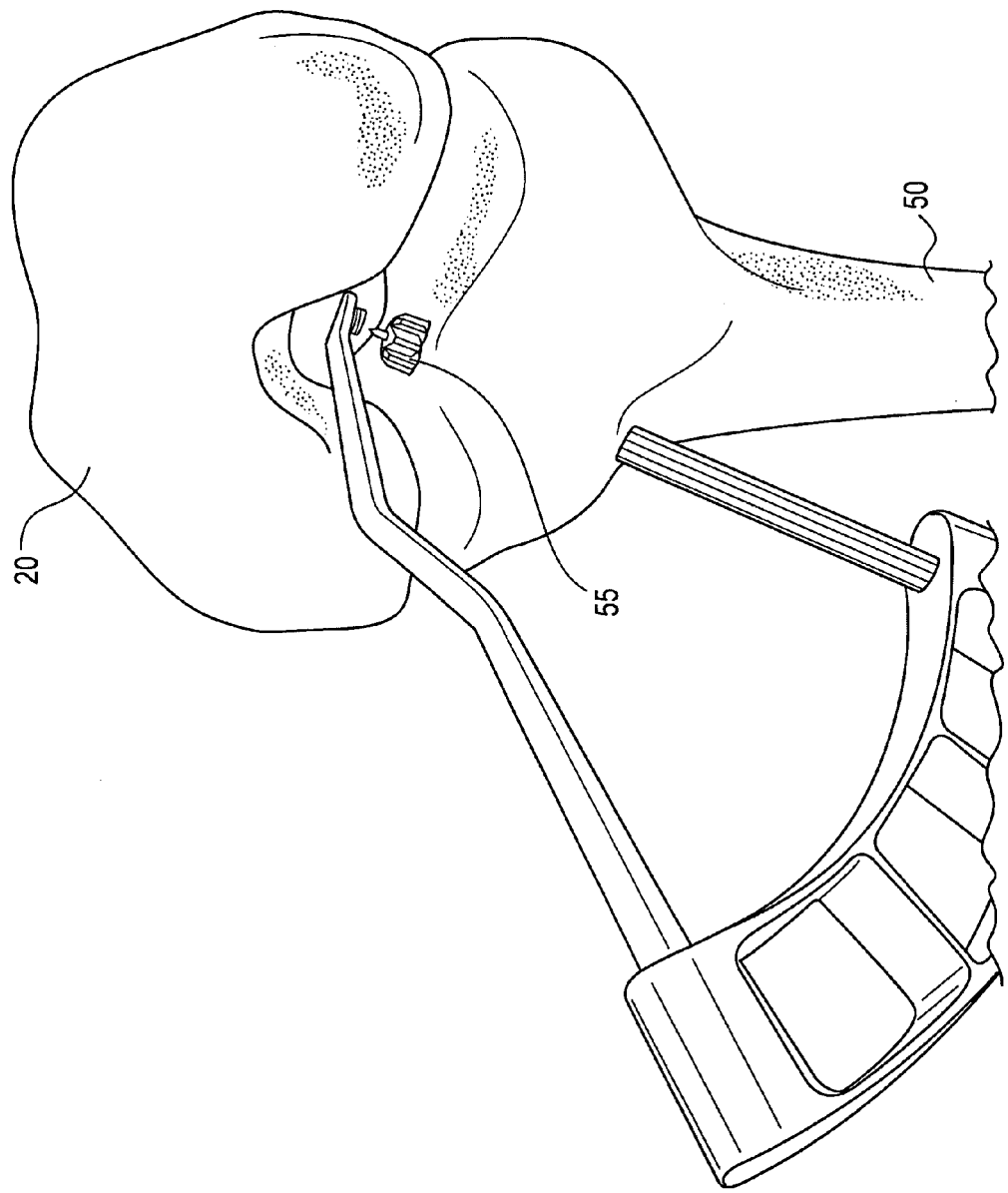
Figure 24:
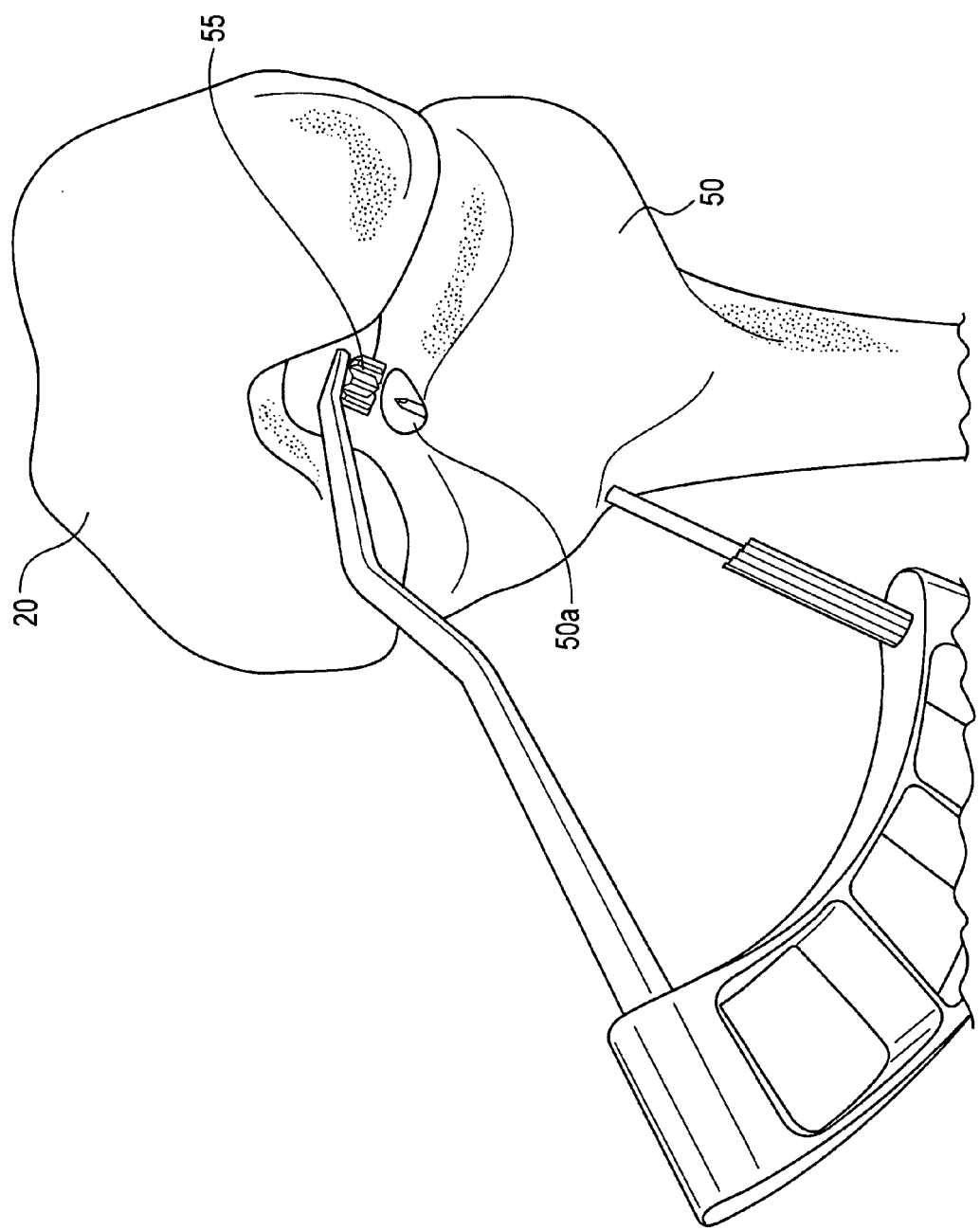
Figure 25:
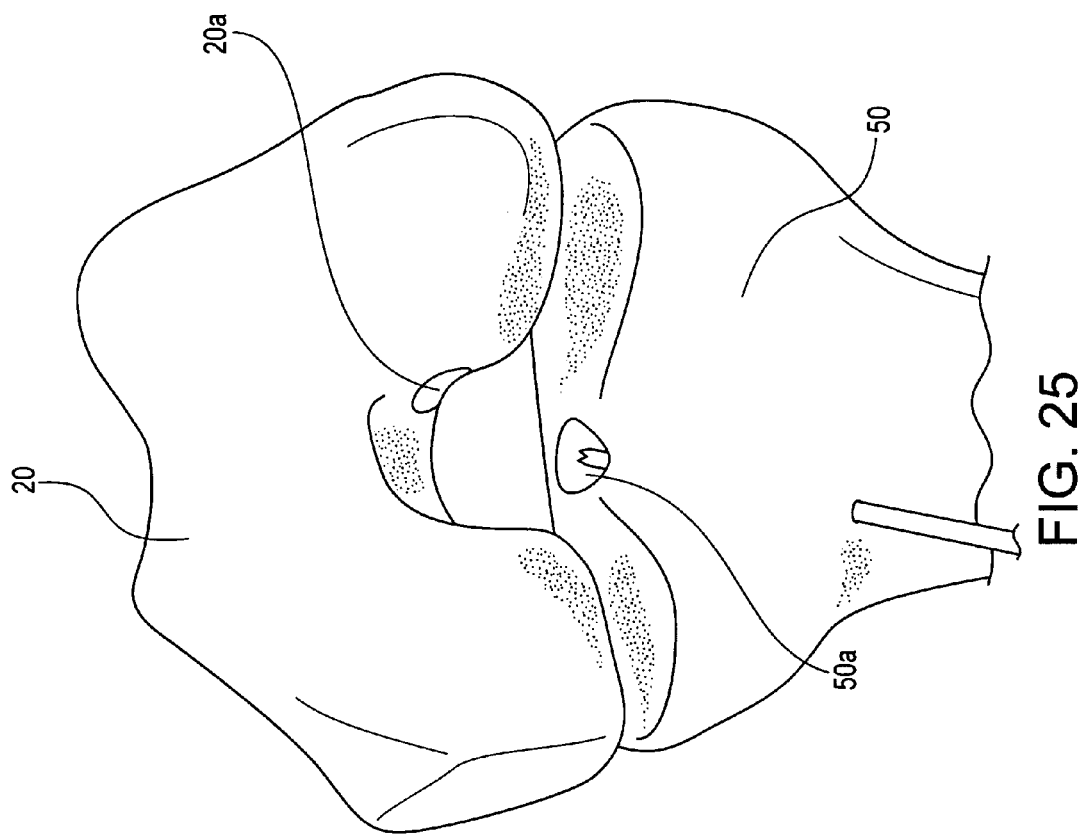
Figure 26:
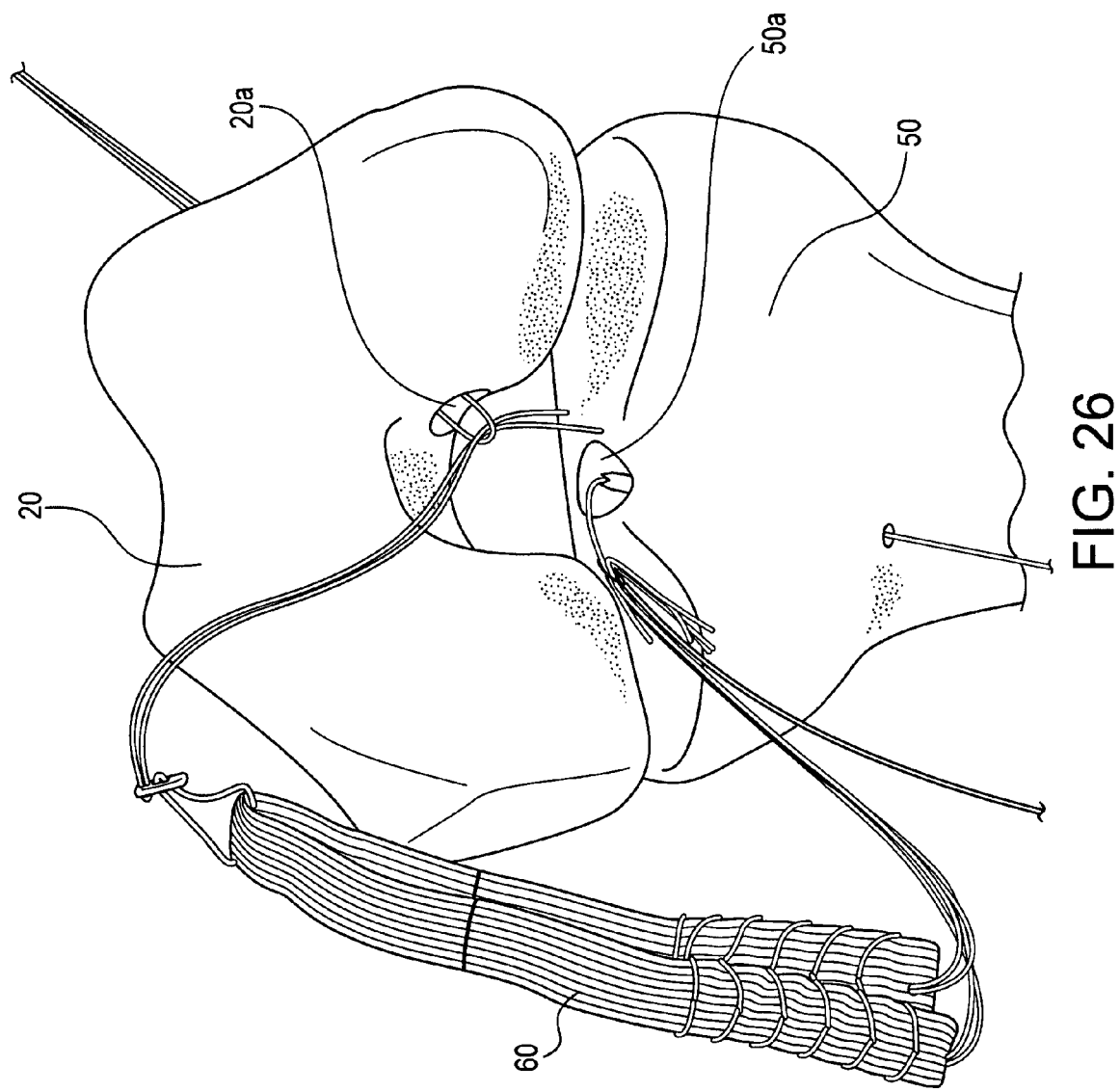
Figure 27:
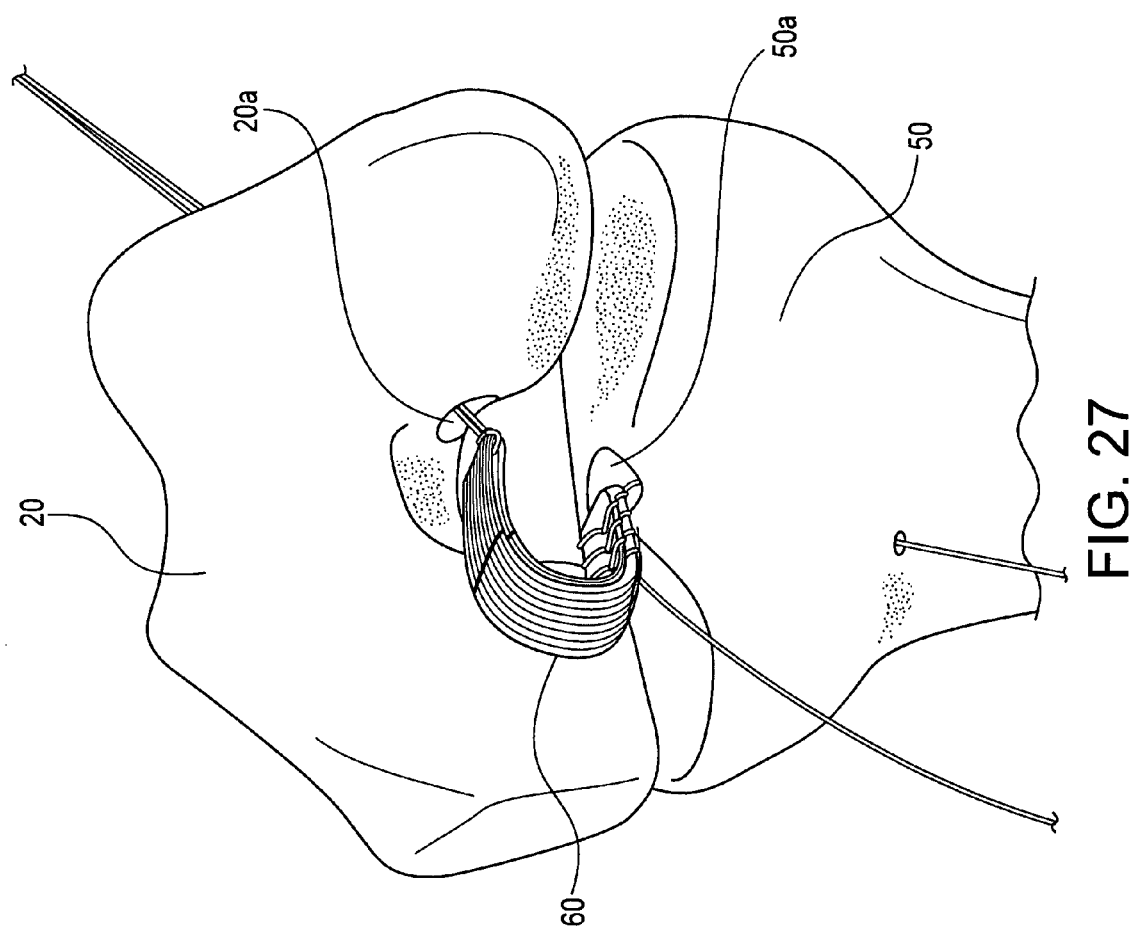
Figure 28:
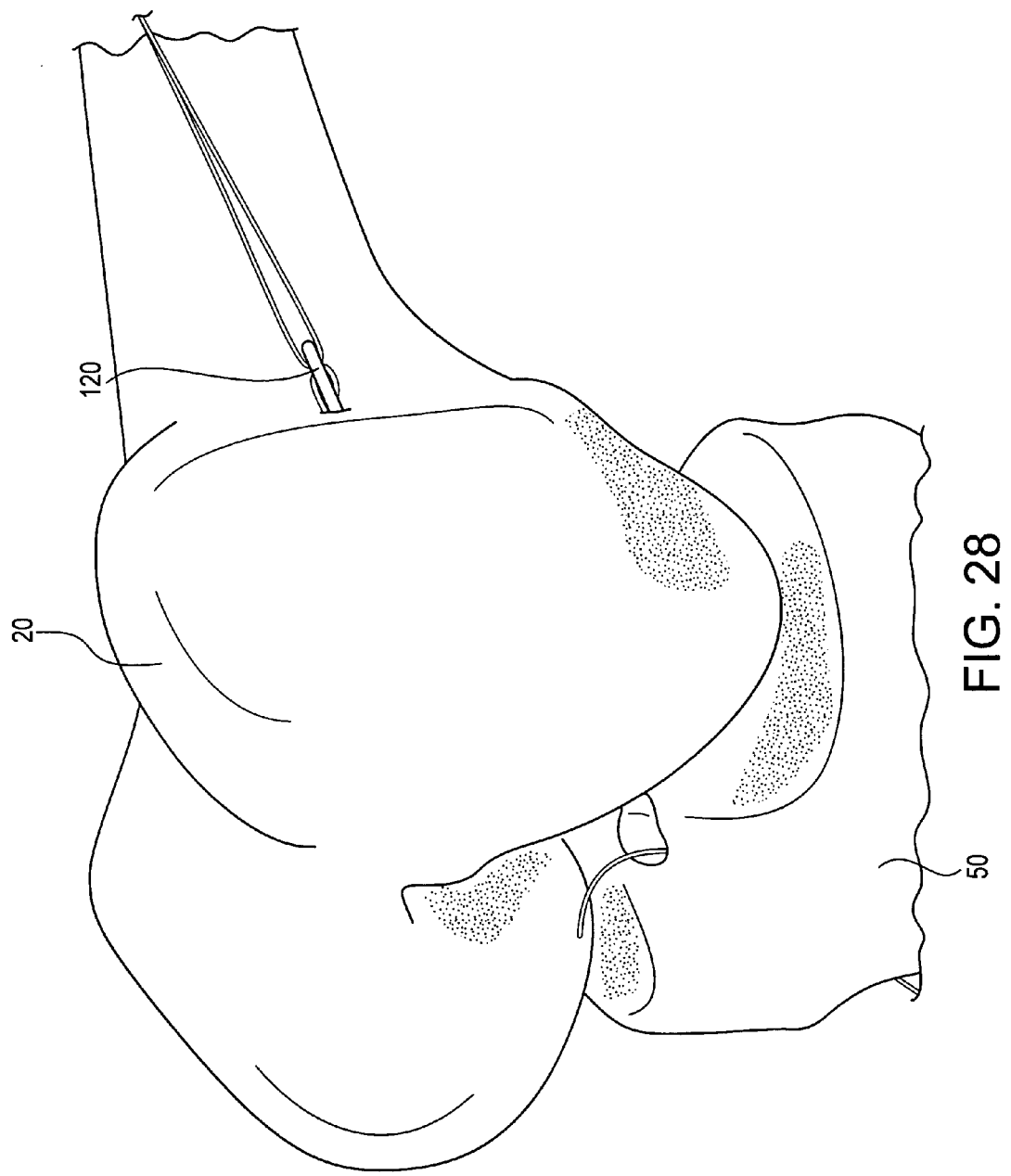
Figure 29:
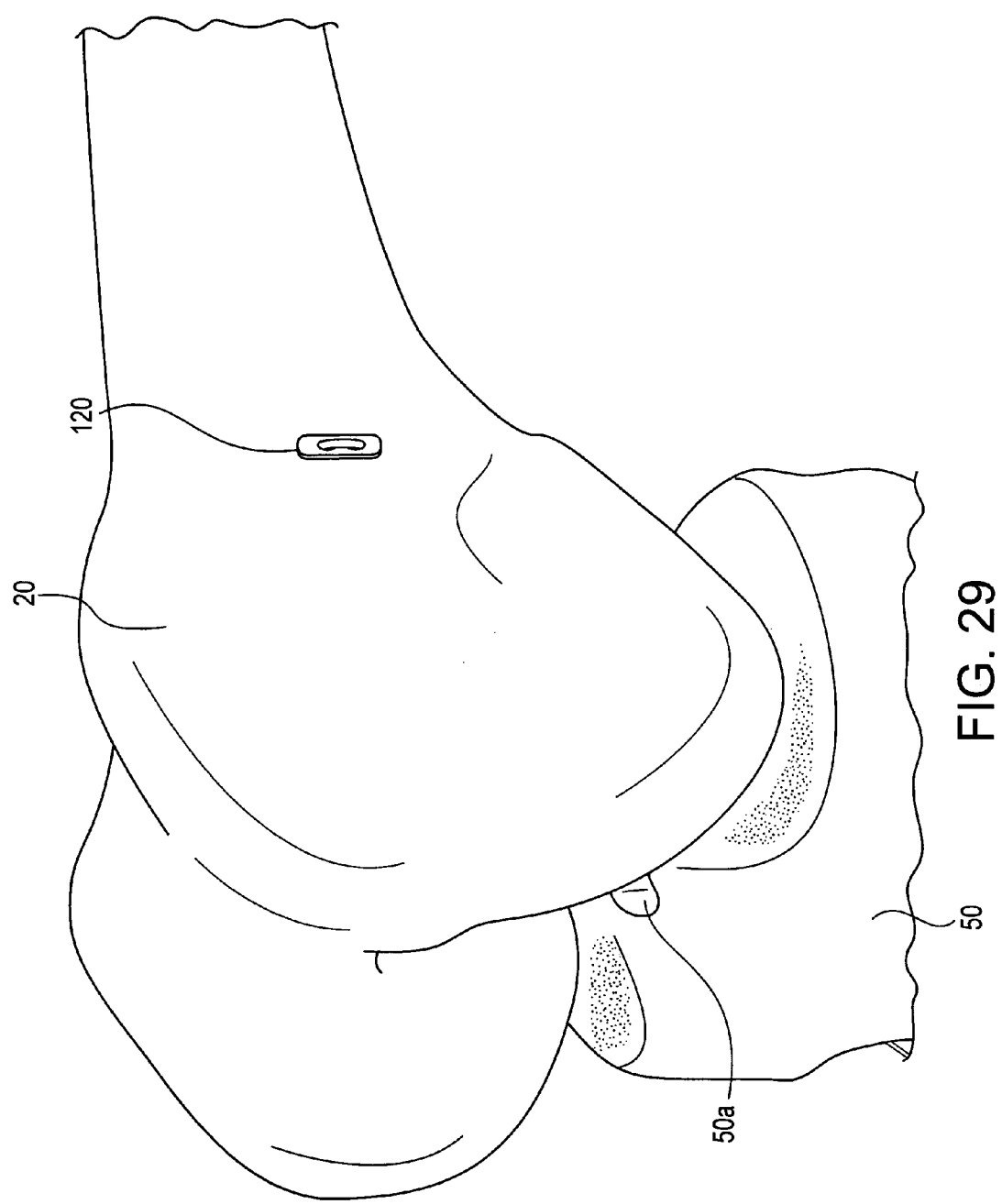
Figure 30:
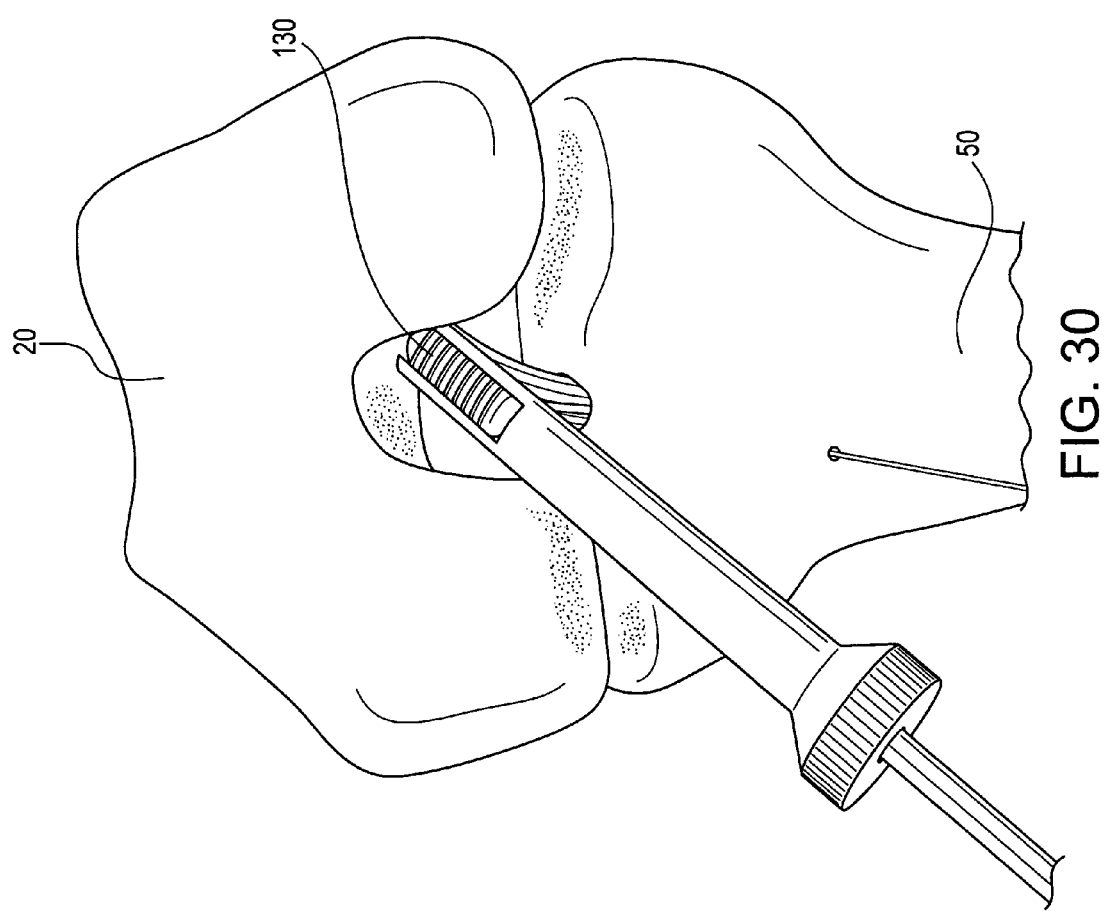
Figure 31:
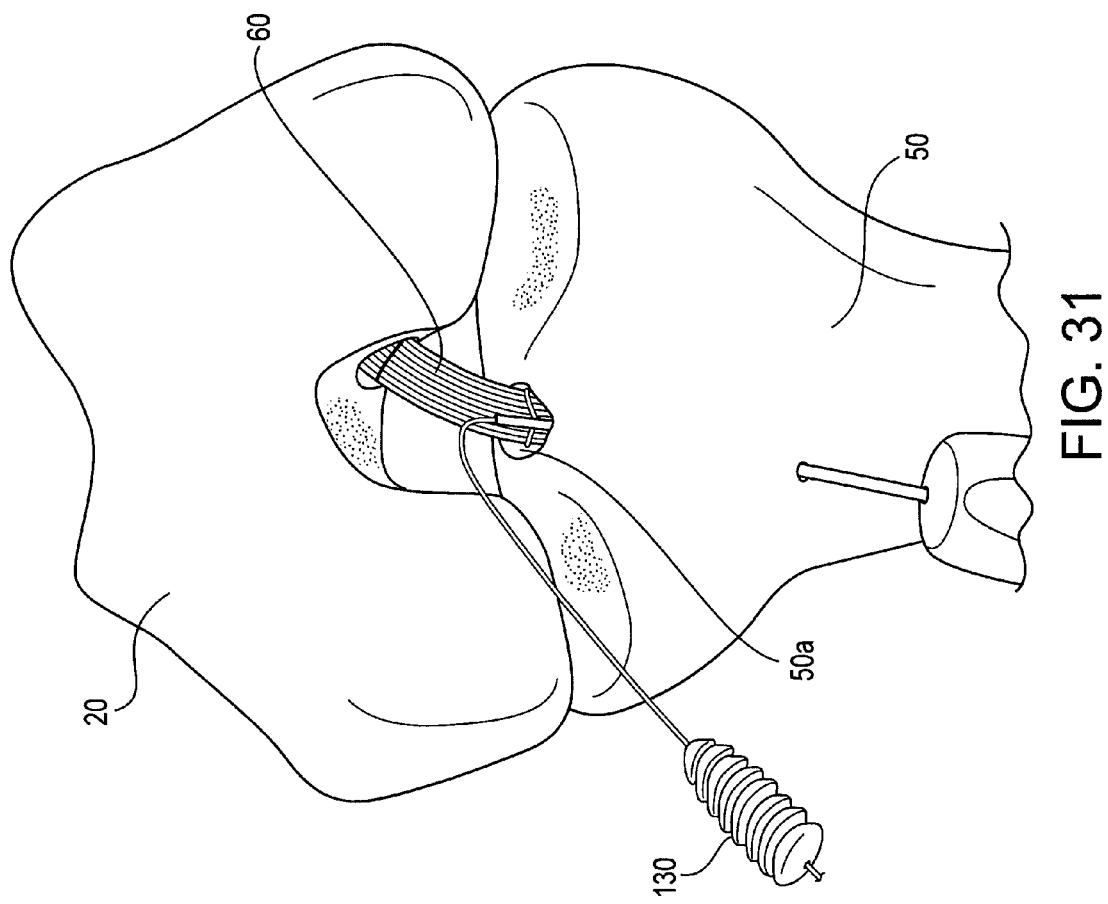

FIG. 18 illustrates the structure of FIG. 11 (with the graft 60 secured in the femoral socket with a medial portal implant 110) and with additional tibial fixation of the graft 60 (with the graft 60 secured in the tibial socket 50*a* with a suture button 120 and a tibial interference screw 130). FIG. 19 illustrates the structure of FIG. 8 (with the graft secured in the femoral socket 20*a* with a suture button 120 and a femoral interference screw 130) and with additional tibial fixation of the graft (with the graft secured in the tibial socket 50*a* with a suture button 120 and a tibial interference screw 130).

Preparation of the graft (for example, a semitendonosus allograft) may be conducted by providing the graft 60 approximately 12 mm shorter than the combined length of the femoral socket, tibial socket and intraarticular space. For suture button (RetroButton): The graft length of the femoral socket is marked. For transversal implant (TransFix): the graft is marked 5 mm less than the length of the femoral socket. The #2 FiberLoop™ is ideal for the all-inside procedure. Stitching such as the SpeedWhip™ technique simplifies whipstitching and compresses and tapers the graft ends to facilitate inside/out graft passing. Use of the SpeedWhip technique allows last minute shortening of graft length.

Figure 32:
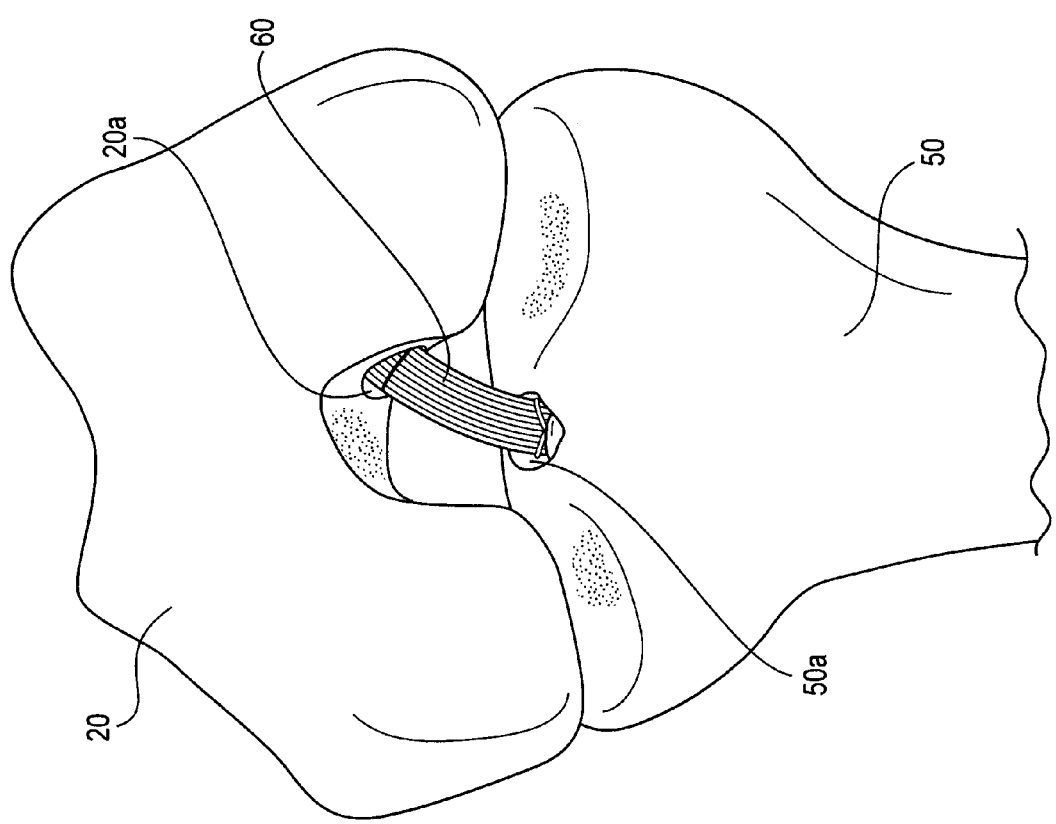

FIGS. 20-32 illustrate detailed steps of an exemplary all-inside double socket ACL reconstruction method for the formation of the structure of FIG. 32 (i.e., an exemplary embodiment wherein the graft is secured in the femoral socket 20*a* with a suture button 120 and an interference screw 130, and in the tibial socket 50*a* with a tibial interference screw 130).

As shown in FIGS. 20-32, and in accordance with an exemplary embodiment only, a femoral socket or tunnel 20*a* (FIG. 21) is formed within femur 20 through the anteromedial portal (as described above) or by a retrograde method. A tibial socket 50*a* is formed in tibia 50 prior or subsequent to the formation of the femoral socket 20*a*, as shown in FIGS. 22-25. The tibial socket 50*a* is preferably formed using a retrodrill cutter 55 (FIGS. 22-24) which is inserted in a retrograde manner through tibia 50, and as detailed in U.S. Patent Application Publication No. 2004/0199166, entitled "ACL Reconstruction Technique Using Retrodrill."

Once the tibial socket 55*a* and the femoral socket 20*a* are formed, the length of the graft 60 (soft tissue grafts and/or BTB grafts) that will be secured within the tibial and femoral sockets is determined based on the entire length of the sockets plus the intraarticular space between them. The selected graft 60 (FIGS. 26-28) is then secured within the femoral tunnel (socket) 20*a* by using the continuous loop/button construct (RetroButton) 120. The other end of the graft 60 may be secured within the tibial socket 50*a* by employing an interference fixation device such as interference screw 130 illustrated in FIG. 31. The final structure shown in FIG. 32 includes graft 60 secured within tibial tunnel (socket) 50*a* (formed in a retrograde manner) by using an interference fixation device (such as interference screw 130), and within femoral socket 20*a* by using a continuous loop/button construct (RetroButton) 120 and another interference fixation device (such as interference screw 130).

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A method of all-inside double socket ACL reconstruction, comprising the steps of:

forming a femoral socket within the femur in an antegrade manner through an anteromedial portal;

forming a tibial socket within the tibia by drilling only part of the tibia, in a retrograde manner, using a rotary drill cutter;

attaching a graft to a suture loop/button construct, the suture loop/button construct comprising a button having at least one eyelet and a continuous suture loop attached to the eyelet, by folding the graft in half over the continuous suture loop;

pulling the graft folded in half over the continuous suture loop and the attached button through the anteromedial portal; and securing one end of the graft within the femoral socket and the other end of the graft within the tibial socket by pulling intraarticularly the suture loop/button construct with the attached graft into the femoral socket, deploying the button so that the button exits the femoral socket and flips horizontally on the cortex, to secure the one end of graft in the femoral socket, and securing the other end of the graft in the tibial socket with at least one of an interference screw and a suture/button construct, wherein the steps of forming the femoral and tibial socket and the step of securing the graft within the femoral and tibial sockets are all conducted in an all-inside manner.

2. The method of claim 1, wherein the suture loop is formed of a suture material comprising ultrahigh molecular weight polyethylene.

3. The method of claim 1, wherein the button has an oblong configuration.

4. The method of claim 1, wherein the rotary drill cutter is a dual-sided rotary drill cutter.

5. The method of claim 1, wherein the rotary drill cutter comprises two opposed sides and is provided with cutting surfaces on both sides, such that the rotary drill cutter is configured for cutting in two directions.

6. The method of claim 1, further comprising:
   attaching the graft to the at least one of an interference screw and a suture loop/button construct; and
   subsequently securing the attached graft within the tibial socket.

* * * * *